(12) United States Patent
Okada et al.

(10) Patent No.: US 6,288,223 B1
(45) Date of Patent: Sep. 11, 2001

(54) PROCESS FOR THE SELECTIVE PREPARATION OF Z-ISOMERS OF 3-2 (SUBSTITUTED VINYL)CEPHALOSPORINS

(75) Inventors: Yumiko Okada; Masamichi Sukegawa; Tatsuo Watanabe, all of Odawara; Hiroyuki Iwasawa, Yokohama; Yasushi Murai; Katsuharu Iinuma, both of Odawara, all of (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/446,380

(22) PCT Filed: Jun. 24, 1998

(86) PCT No.: PCT/JP98/02820

§ 371 Date: Feb. 18, 2000

§ 102(e) Date: Feb. 18, 2000

(87) PCT Pub. No.: WO98/58932

PCT Pub. Date: Dec. 30, 1998

(30) Foreign Application Priority Data

Jun. 24, 1997 (JP) .................................................... 9-166948

(51) Int. Cl.⁷ ...................... C07D 501/04; C07D 501/12; C07D 501/24

(52) U.S. Cl. ........................... 540/220; 540/226; 540/227

(58) Field of Search .................................. 540/226, 227, 540/220

(56) References Cited

U.S. PATENT DOCUMENTS 5,616,703 * 4/1997 Ludescher ............................ 540/226

FOREIGN PATENT DOCUMENTS

| 62-19593 | 1/1987 | (JP) . |
|---|---|---|
| 3-128382 | 5/1991 | (JP) . |
| 7-188250 | 7/1995 | (JP) . |
| 8-67684 | 3/1996 | (JP) . |

* cited by examiner

Primary Examiner—Mark L. Berch
(74) Attorney, Agent, or Firm—Larson & Taylor PLC

(57) ABSTRACT

There can be produced, at a high selectivity and in a high yield, the Z-isomer of a 7-N-unsubstituted or substituted-amino-3-[2-(4-substituted or unsubstituted-thiazol-5-yl) vinyl]-3-cephem-4-carboxylic acid or an ester thereof having the general formula (IV)

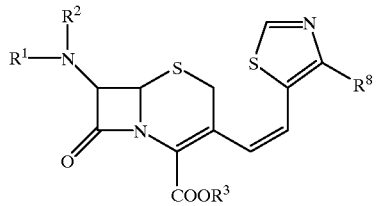

(IV)

wherein $R^1$ denotes a hydrogen atom, a mono-valent amino-protecting group or a 2-(2-N-protected or unprotected aminothiazol-4-yl)- 2-alkoxyiminoacetyl group, $R^2$ denotes a hydrogen atom, or $R^1$ and $R^2$ as taken together mean one di-valent amino-protecting group, $R^3$ denotes a hydrogen atom, pivaloyloxymethyl group or a carboxyl-protecting group and $R^8$ denotes an alkyl group and so on, by a process comprising reacting a 7-N-unsubstituted or substituted-amino-3-[(tri-substituted-phosphoranylidene) methyl]-3-cephem-4-carboxylic acid or an ester thereof having the general formula (I)

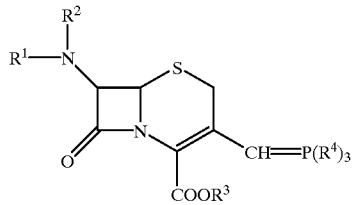

(I)

wherein $R^1$, $R^2$ and $R^3$ each have the same meanings as defined above, and $R^4$ denotes a lower alryl group or an aryl group, with a 4-substituted or unsubstituted-thiazol-5-carbaldehyde in a mixed solvent consisting of a mixture of one or more chlorinated hydrocarbon solvent(s) with one or more lower alkanol(s) at a low temperature of +5° C. or below. According to the processes of this invention, the production of such E-isomer of the compound (IV) that is of lower antibacterial activity than that of the Z-isomer can be suppressed remarkably. Further, the Z-isomer of a high purity can be produced efficiently in a facile way.

10 Claims, No Drawings

PROCESS FOR THE SELECTIVE PREPARATION OF Z-ISOMERS OF 3-2 (SUBSTITUTED VINYL)CEPHALOSPORINS

TECHNICAL FIELD

This invention relates to a novel process for producing selectively and in a high yield the Z-isomer (cis-isomer) of a cephalosporin antibiotic having a 2-(4-substituted or unsubstituted-thiazol-5-yl)vinyl group as the 3-substituent, or the Z-isomer (cis-isomer) of such a 7-amino-3-[2-(4-substituted or unsubstituted-thiazol-5-yl)vinyl]-3-cephem-4-carboxylic acid or a protected derivative thereof which is utilizable as an intermediate for the synthesis of the said cephalosporin antibiotic. This invention also relates to a novel process for producing efficiently and in a facile way a highly pure Z-isomer (cis-isomer)of a 7-[2-(2-aminothiazol-4-yl)-2-alkoxyiminoacetamido]-3-[2-(4-substituted or unsubstituted-thiazol-5-yl)vinyl]-3-cephem-4-carboxylic acid, or a 7-amino-3-[2-(4-substituted or unsubstituted-thiazol-5-yl)vinyl]-3-cephem-4-carboxylic acid or a protected derivative thereof.

BACKGROUND ART

Japanese Patent Publication No. Hei 3-64503 (Japanese Patent No. 1698887), U.S. Pat. No. 4,839,350 or European Patent No. 0175610 specification discloses 7-[2-methoxyimino-2-(2-amino-thiazol-4-yl)acetamido]-3-[2-(4-methylthiazol-5-yl)vinyl]-3-cephem-4-carboxylic acid (syn-isomer, cis-isomer) represented by the following formula (A)

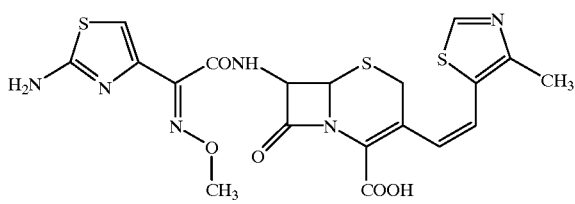

(A)

This compound is an excellent cephalosporin antibiotic called as "Cefditoren". The excellent antibacterial activity of Cefditoren against gram-negative bacteria is attributable to the fact that the Cefditoren compound has the Z-configuration such that the cephem ring and the 4-methylthiazol-5-yl group of Cefditoren are connected in the cis-configuration to the carbon-carbon double bond of the 3-vinyl group of the Cefditoren molecule.

7-[2-Methoxyimino-2-(2-aminothiazol-4-yl)acetamido]-3-[2-(4-methylthiazol-5-yl)vinyl]-3-cephem-4-carboxylic acid pivaloyloxymethyl ester (syn-isomer, cis-isomer), which is derived by esterifying the 4-cartboxyl group of the above-mentioned Cefditoren compound with pivaloyloxymethyl group, is represented by the following formula (B)

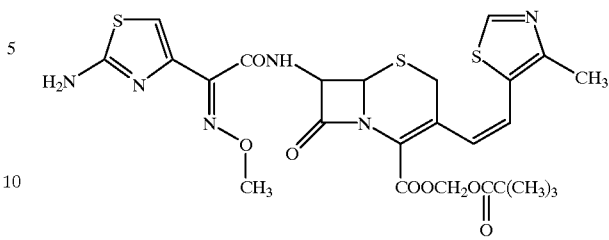

(B)

and is a pro-drug known as a general name "Cefditoren pivoxil" (refer to "Merck Index" 12th Edition, Page 317). In cases of the 3-(2-substituted-vinyl)-cephalosporin antibiotics, it is generally known that the Z-isomer (cis-isomer) is superior to the E-isomer (trans-isomer) in the various properties of the antibiotics.

The above-mentioned 3-(2-substituted-vinyl)-cephalosporin antibiotics including Cefditoren, or intermediates usable for the synthesis of said antibiotics may be prepared by various processes. As one of the processes available for the production of these antibiotics, there is known a process using Wittig's reaction. Such a process for the preparation of the 3-(2-substituted-vinyl)-cephalosporin antibiotics or the intermediates for their synthesis which comprises using Wittig's reaction is disclosed, for example, in Japanese Patent Application first publication KOKAI Hei-3-264590 or the corresponding U.S. Pat. No. 5,233,035 or European Patent Application Publication No. 0175610A2; the "Journal of Antibiotics" XLIII, No. 8, pages 1047–1050 (1990), "Chem. Pharm. Bull." Vol. 39, No. 9, pages 2433–2436(1991), and international Publication No. WO95/09171 (published on Apr. 6, 1995) of PCT Application No.PCT/JP94/01618 or the corresponding European Patent Application Publication No. 0734965A1 specification. By conducting the Wittig's reaction step in accordance with the prior art processes, the resultant reaction product has always been given in the form of a mixture of the Z-isomer and E-isomer of the produced compound.

For example, the "Journal of Antibiotics" XLIII, No. 8, pages 1047–1050 and "Chem. Pharm. Bull." Vol. 39, No. 9, pages 2433–2436 mentioned above disclose a process for the preparation of such 4-methoxybenzyl ester of 7-β-phenylacetamido-3-[2-(4-methylthiazol-5-yl)vinyl]-3-cephem-4-carboxylic acid, which may be used for the synthesis of the aforesaid 7-[(Z)-2-(2-aminothiazol-4-yl)-2-methoxyirnino-acetamido]-3-(Z)-(4-methylthiazol-5-yl) vinyl-3-cephem-4-carboxylic acid. In this process, there are carried out the steps of treating p-methoxybenzyl ester of 7-β-phenylacetamido-3-chloromethyl-3-cephem-4-carboxylic acid with sodium iodide in acetone to produce the corresponding 3-iodomethyl derivative; treating this derivative with triphenylphosphine to produce the corresponding triphenylphosphonium iodide derivative; and reacting this triphenylphosphonium iodide derivative with 5-formyl-4-methylthiazol by the Wittig's reaction at room temperature in a heterogeneous reaction medium comprising dichloromethane (i.e. methylene chloride) and water in the presence of sodium hydrogen carbonate, thereby to produce the 4-methoxybenzyl ester of 7-β-phenylacetamido-3-[2-(4-methylthiazol-5-yl)vinyl]-3-cephem-4-carboxylic acid.

The above-mentioned process may be expressed by the following reaction scheme:

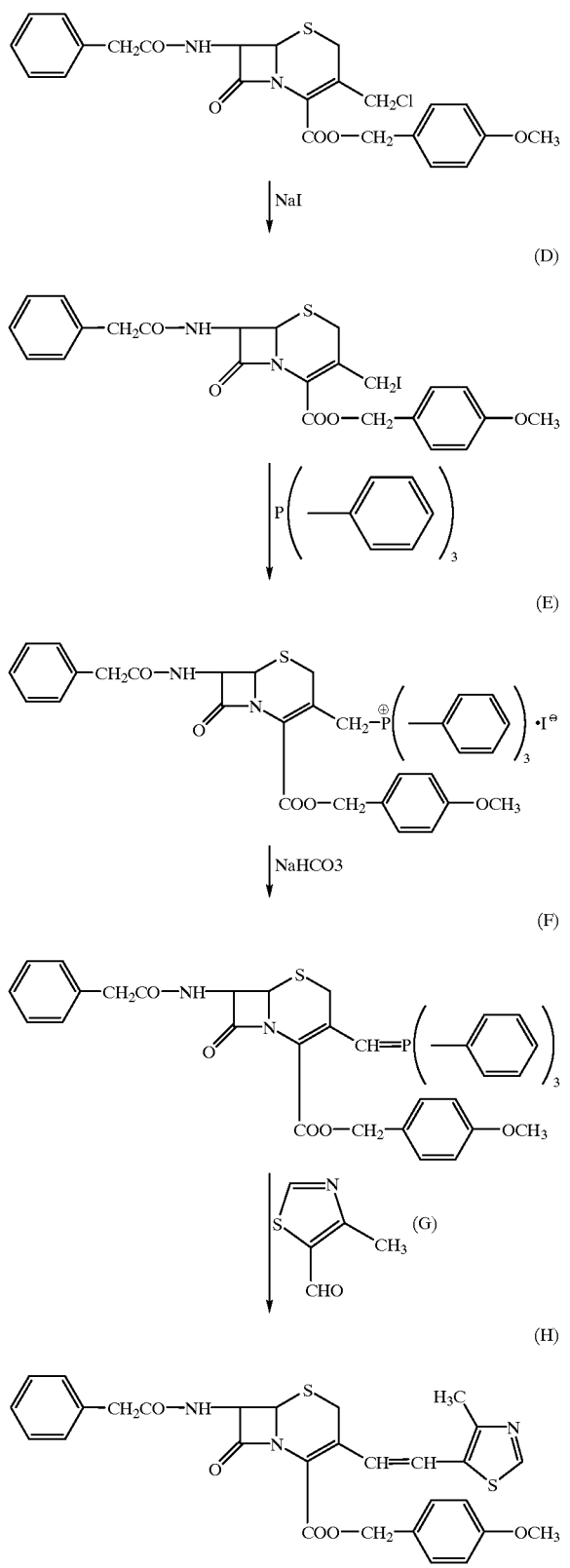

In the above-mentioned process, there is produced, as an intermediate product, 4-methoxybenzyl ester of 7-β-phenylacetamido-3-[(triphenylphosphoranylidene)methyl]-3-cephem-4-carboxylic acid of formula (F) above, which is then reacted with 5-formyl-4-methylthiazole by the Wittig's reaction to produce 4-methoxybenzyl ester of 7-β-phenylacetamido-3-[2-(4-methylthiazol-5-yl)vinyl]-3-cephem-4-carboxylic acid of formula (H). The reaction product of formula (H) is described in the above-mentioned literature to have been obtained in the form of a mixture of the Z-isomer (cis-isomer) and E-isomer (trans-isomer) of the compound (H) at a mix ratio of 4.7:1.

The above literature "Journal of Antibiotics" describes that the mixed Z-isomer and E-isomer of the compound of formula (H) is difficult to be isolated from each other even by treating with a column chromatographic technique. Then, said literature further discloses that the Z-isomer of the target product could be isolated only by effecting amethod comprising removing the 7-phenylacetyl group fro:m the compound of formula (H) by a deprotection technique, condensing the 7-position of the deprotected product with 2-(2-tritylaminothiazol-4-yl)-2-methoxyimino-acetic acid, subjecting the resulting condensation product to a deprotection reaction, then subjecting the resulting deprotected product to a column chromatography with a non-ionic porous resin, and further subjecting the resulting product so purified to a fractional crystallization. Thus, the yield of the desired Z-isomer as finally harvested was necessarily low to a considerable extent.

Further, Japanese Patent Application First Publication KOKAI Hei-7–188250 or the corresponding U.S. Pat. No. 5,616, 703 or European Patent Application Publication No. 658558A1 specification discloses that the reaction product, which comprised 7-amino-3-[2-(4-methylthiazol-5-yl)vinyl]-3-cephem-4-carboxylic acid or a derivative thereof having the following formula (J)

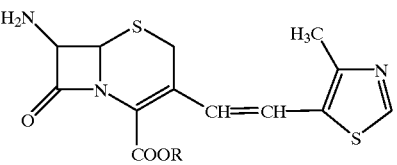

where R is a protecting group of silyl type or a hydrogen atom and which was produced by the Witting's reaction, is a mixture of the Z-isomer and E-isomer. The Japanese Patent Application First Publication KOKAI Hei-7-188250 specification also discloses a method for the isolation of the Z-isomer which comprises converting the Z/E mixture of 7-amino-3-[2-(4-methylthiazol-5-yl)vinyl]3-cephem-4-carboxylic acid into a corresponding amine salt and subjecting the amine salt so obtained to a recrystallization step. This Publication further discloses that when the said Z/E mixture is subjected to a chromatography, there can be obtained the Z-isomer from which the E-isomer of a lower activity has been removed as much as possible.

Further, the above-mentioned PCT International Publication No. WO95/09171 discloses a process which comprises the steps of treating a phosphonium halide compound represented by the following formula (K)

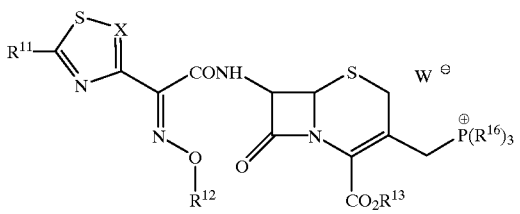

(K)

where X is CH or N, $R^{11}$ is an amino group or a protected amino group, $R^{12}$ is a hydrogen atom or a hydroxyimino-protecting group, $R^{13}$ is a hydrogen atom, a salt-forming cation or a carboxyl-protecting group, $R^{16}$ is an aryl group, for example, a phenyl group, and W is a halogen atom, with a base such as sodium hydrogen carbonate in acetone, tetrahydrofuran, methylene chloride or water at room temperature, to produce a tri-aryl phosphoranylidene compound represented by the following formula (L)

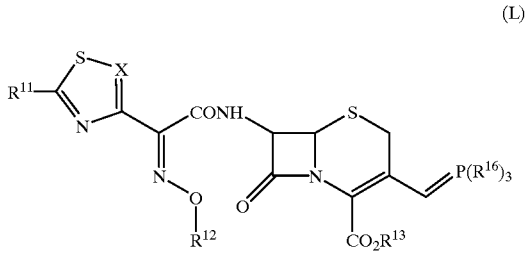

(L)

where $R^{11}$, $R^{12}$, $R^{13}$ and $R^{16}$ have the same meanings as defined above, then reacting the compound of formula (L) with a 4-substituted or unsubstituted-thiazol-5-carbaldehyde of the following formula (G')

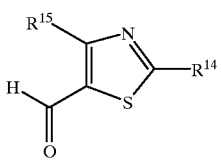

(G')

where $R^{14}$ is a hydrogen atom, $R^{15}$ is a hydrogen atom, a lower alkyl group, a halo-lower alkyl group or a halogen atom, by the Wittig's reaction at room temperature or under cooling in methylene chloride, methylene chloride-water, tetrahydrofuran or dioxane, to produce a 3-vinyl-cephem compound represented by the following formula (N)

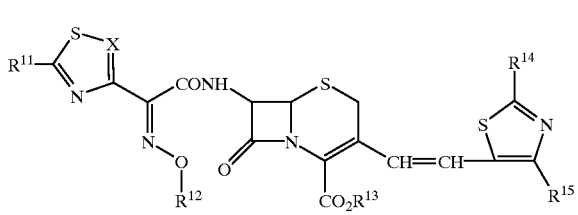

(N)

where $R^{11}$, $R^{12}$, $R^{13}$, $R^{14}$ and $R^{15}$ have the same meanings as defined above. In this prior art process, the resultant reaction product which comprises the 3-vinyl-cephem compound of formula (N) as obtained by reacting the phosphoranylidene compound of formula (L) with the aldehyde compound of formula (G') through the Wittig's reaction, was also in the form of a mixture of Z-isomer (cis-isomer) and E-isomer (trans-isomer) of the compound (H). In order to isolate and recover the desired Z-isomer from the 3-vinyl-cephem compound of formula (N), it was necessary for the above-mentioned process that the reaction solution as obtained from the Wittig's reaction step was at first washed with an aqueous sodium chloride solution, then dried over anhydrous magnesium sulfate and further concentrated under a reducedl pressure and that the resulting concentrate residue was further purified by a chromatography so as to separate thes Z-isomer from the E-isomer. Thus, in this prior art process, the yield of the desired Z-isomer of the 3-vinyl-cephem compound of formula (N) was, in fact, not satisfactorily high, too. With the prior art processes for the production of the 3-vinyl-cephem compound which comprise using the Wittig's reaction, there cannot be found any precedent case where a lower alkanol is used in the reaction medium for the Wittig's reaction.

Therefore, when there has been carried out the process for the production of a cephalosporin compound having the 3-[2-(4-substituted or unsubstituted-thiazol-5-yl)vinyl group which comprises reacting such a 7-[2-(2-aminothiazol-4-yl) 2-alkoxyiminoacetamido]-[3-(tri-substituted-phosphoranylidene) methyl]-3-cephem-4-carboxylicacid or an ester thereof as embraced by the compound of formula (L) above, or a 7-amino-or 7-N-protected amino-3-[(tri-substituted-phosphoranylidene) methyl]-3-cephem-4-carboxylic acid or an ester thereof, with a 4-substituted or unsubstituted-thiazol-5-carbaldehyde of formula (G') through the Wittig's reaction, there has been presented a demand for providing such a novel process for the production of the 3-(2-substituted-vinyl)-cephalosporin compounds which would be capable of producing selectively the desired Z-isomer (cis-isomer) of the 3-(2-substituted-vinyl)-cephalosporin compounds in a significantly higher proportion than that of the undesirable E-isomer (trans-isomer) of the 3-(2-substituted-vinyl)-cephalosporin compounds.

It has also been presented a demand for providing such a novel process for the production of the 3-(2-substituted-vinyl)-cephalosporins which would be capable of recovering the desired Z-isomer of the final cephalosporin product in a high yield and at a high purity directly from the resulting reaction solution of the Wittig's reaction, without involving any necessity to carry out any further specific purification step for separating the desired Z-isomer from the E-isomer as formed.

DISCLOSURE OF INVENTION

Thus, the prior art processes fcr the production of the 3-(2-substituted-vinyl)-cephalosporin, which comprises using the Wittig's reaction, have such various drawbacks that the selectivity of the production of the Z-isomer is poorer as compared with that of the E-isome, that the isolation of the Z-isomer from the E-isomer has required some additional and complicated operations, and that the actual yield of the Z-isomer is unsatisfactorily low.

Further, in practising the above-mentioned prior art processes, there was employed the conventional procedure such that the step of the Wittig's reaction was carried out with using, in substantially all cases, methylene chloride or methylene chloride-water as the reaction medium, and with using the room temperatures for the reaction temperature.

We, the present inventors, have carried out our extensive investigations with the intention of providing such a novel process for the production of the 3-(2-substituted-vinyl)-cephalosporins which is free from the drawbacks of the prior art processes as mentioned above. In particular, we have concentrically studied on the reaction medium, reaction temperature and other reaction conditions which are available for Wittig's reaction. As a result, we now have surprisingly found that, if a mixed solvent consisting of a mixture of a chlorinated hydrocarbon solvent with a lower alkanol as mixed at a certain mix ratio (by volume) is used as the reaction medium for the Wittig's reaction, and if, simultaneously, a temperature of 5° C. or below, preferably of 0° C.~−50° C. is used as the reaction temperature for the Wittig's reaction, it is feasible to produce the desired Z-isomer of the 3-(2-substituted-vinyl)-cephalosporin, in a significantly higher larger proportion than that of the undesirable E-isomer in the reaction solution of the Witting's reaction, so that the selectivity of the production of the desired Z-isomer is thus improved and the yield of the Z-isomer is enhanced. On the basis of these our findings, we have completed this invention.

According to a first aspect of this invention, therefore, there is provided a process for the selective production of the Z-isomer of a 7-N-unsubstituted or substituted-amino-3-[2-(4-substituted or unsubstituted-thiazol-5-yl)vinyl]-3-cephem-4-carboxylic acid or an ester thereof represented by the following general formula (IV)

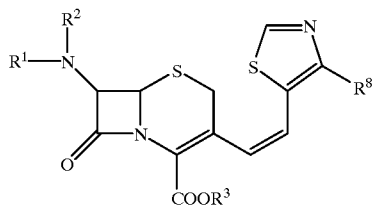

(IV)

wherein $R^1$ denotes a hydrogen atom or a mono-valent amino-protecting group, or $R^1$ denotes a 2-(2-N-protected or unprotected-aminothiazol-4-yl)-2-alkoxyiminoacetyl group having the following formula (II)

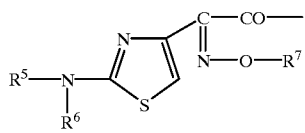

(II)

where $R^5$ is a hydrogen atom or a mono-valent amino-protecting group and $R^6$ is a hydrogen atom, or $R^5$ and $R^6$ as taken together mean a di-valent amino-protecting group and $R^7$ is an alkyl group of 1~4 carbon atoms and wherein $R^2$ denotes a hydrogen atom, or $R^1$ and $R^2$ as taken together mean a di-valent amino-protecting group and $R^3$ denotes a hydrogen atom, pivaloyloxymethyl group or an ester-forming group as a carboxyl-protecting group, and $R^8$ denotes a hydrogen atom, an alkyl group of 1~4 carbon atoms, trifluoromethyl group or a chloro group, characterized in that said process comprises reacting a 7-N-unsubstituted or substituted-amino-3-[(tri-substitutesd-phosphoranylidene) methyl]-3-cephem-4-carboxylic acid or an ester thereof represented by the following generaL formula (I)

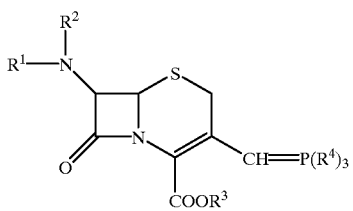

(I)

where $R^1$, $R^2$ and $R^3$ each have the selme meanings as defined above and $R^4$ denotes an alkyl group of 1~6 carbon atoms or an aryl group, or a compound represented by the following general formula (I')

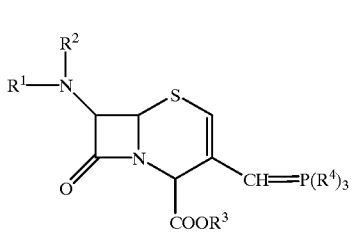

(I')

where $R^1$ $R^2$, $R^3$ and $R^4$ each have the same meanings as defined above, with a 4-substituted or unsubstituted-thiazol-5-carbaldehyde represented by the following formula (III)

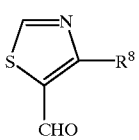

(III)

where $R^8$ has the same meaning as defined above, in a mixed solvent consisting of one or more chlorinated hydrocarbon solvent(s) and one or more lower alkariol(s) as mixed together at a mix ratio (by volume) in a range of from 1:3 to 1:0.25, at a temperature of +5° C. to −50° C.

The process according to the first aspect of this invention is different from the aforesaid prior art processes for the production of the 3-(2-substituted-vinyl)-cephalosporins with using the Wittig's reaction in that the process of this invention employs as the reaction medium such a mixed solvent made of a mixture of the chlorinated hydrocarbon solvent(s) with the lower alkanol(s) as mixed together at a certain specific mixing ratio, and that the process of this invention employs as the reaction temperature a temperature of 5° C. or lower. However, the process of this invention has no significant differences in respect of the other reaction procedures and reaction conditions from those of the prior art processes. In spite of such small differences over the prior art processes, the process of this invention can achieve the production of the desired Z-isomer of the cephem compounds of formula (IV) in a higher selectivity and at a higher yield than the E-isomer. This is quite unexpectable.

The compound of general formula (I) which is used as the starting material in the process of the first aspect of this invention may be prepared by a method comprising the steps of (i) treating a 3-halomethyl-3-cephem compound of the followimg general formula (V)

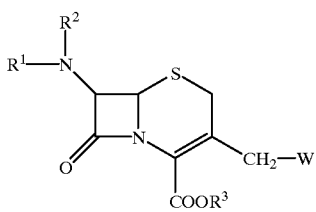

(V)

where $R^1$, $R^2$ and $R^3$ each have the same meanings as defined above and W is a chlorine atom or a bromine atom, with sodium iodide or potassium iodide in a reaction medium, for example, acetone or a mixed solvent made of a mixture of methylene chloride or chloroform with water at room temperature, to produce a 3-iodomethyl-3-cephem compound of the following general formula (VI)

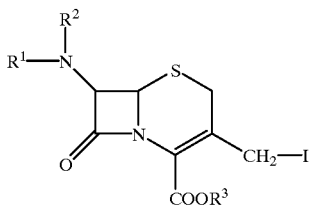

(VI)

where $R^1$, $R^2$ and $R^3$ each have the same meanings as defined above; (ii) reacting the compound o: formula (VI) with a tri-alkylphosphine or a tri-arylpho.,phine of the following formula (VII)

(VII)

Where R4 is an alkyl group of 1~6 carbon atoms, preferably a straight chain alkyl group, or an aryl group, preferably phenyl group or a ($C_1$~$C_4$)alkyl-substituted phenyl group, in a reaction medium of the nature same as that used in the step (i) above at room temperature, to produce a tri-alkyl (or aryl)phosphonium-methyl compound of the following general formula (VIII)

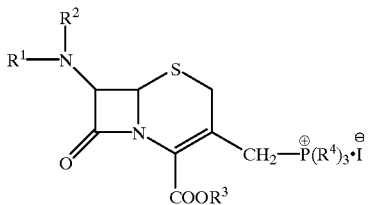

(VIII)

where $R^1$, $R^2$, $R^3$ and $R^4$ each have the same meanings as defined above; and (iii) reacting the phosphonium-methyl compound of formula (VIII) with an aqueous solution of a base such as sodium hydrogen carbonate or sodium hydroxide in a reaction medium made of, for example, methylene chloride or chloroform-water at room temperature or under ice-cooling to produce the tri-alkyl (or aryl) phosphoranylidene compound of the general formula (I) shown above. As the starting compound, a compound of general formula (I') may be used instead of the compound of general formula (I) above. It is convenient that the reaction solution which was obtained in the step (iii) above and containing the compound of general formula (I) is used as such directly in the process of this invention, so that the process of this invention may continue as "one pot" process, without separation of the compound of general formula (I) from the reaction solution of the said step (iii) of preparing the compound (I).

In the compound of general formula (I) or (I') used as the starting compound, the mono-valent amino-protecting group, which may be represented by $R^1$ and(or) $R^5$, has no particular limitation, so far as it is such an amino-protecting group as conventionally used in the synthesis of penicillin and cephalosporin compounds.

As examples of such mono-valent amino-protecting groups, there may be listed a substituted or unsubstituted mono(or di or tri)-phenylalkyl group, for example, benzyl group, benzhydryl group, trityl group; an alkanoyl group, for example, formyl group, acetyl group; a lower allcoxycarbonyl group, for example, methoxycarbonyl group; an aromatic acyl group, for example, benzoyl group, tolyl group; heterocyclic carbonyl group, for example, thiazolylcarbonyl group, tetrazolylcarbonyl group; an alkanoyl group substituted with an aryl or aryloxy group, for example, phenylacetyl group, phenoxyacetyl group; an aralkyloxycarbonyl group, for example, benzyloxycarbonyl group; or an alkanoyl group substituted by a heterocyclic group, for example, imidazolylacetyl group, thiazolylacetyl group; and the like. Phenylacetyl group is particularly preferred as the amino-protecting group. In cases where $R^1$ and $R^2$, or $R^5$ and $R^6$ as taken together mean one di-valent amino-protecting group, examples of such di-valent amino-protecting group are a substitutedorunsubstitutedaralkylidene group, for example, benzylidene group, salicylidene group and etrahydro-pyranylidene group.

Further, in such compounds of general formula (I) or (I') where $R^3$ represents an ester-forming group as the carboxyl-protecting group, such ester-forming group has no particular limitation, so far as it is such a carboxyl-protecting group available at the 3-position or the 4-position of penicillins and cephalosporins in their synthesis. As such ester-forming groups for $R^3$, there are exemplified a lower alkyl group, for example, methyl group, ethyl group, t-butyl group; a lower alkenyl group, for example, vinyl group, allyl group; a lower alkoxyalkyl group, for example, methoxymethyl group, ethoxymethyl group; alower alkylthioalkyl group, forexample, methylthiomethyl group, ethylthiomelhyl group; a lower alkanoyloxyalkyl group, for example. acetoxymethyl group, butylyloxymethyl group; substituted or unsubstituted mono(or di or tri)-phenylalkyl group, for example, benzyl group, 4-methoxybenzyl group, benzhydryl group, trityl group, and the like. 4-Methoxybenzyl group is particularly preferred as said carboxyl-protecting group.

Further, $R^4$ represents a lower alkyl group or an aryl group. The lower alkyl group for $R^4$ may be an alkyl group of 1~6 carbon atoms, particularly methyl group, ethyl group, propyl group, n- or t- butyl group. Particularly preferred is n-butyl group. As an aryl group for $R^4$, phenyl group is particularly preferred.

Examples of the chlorinated hydrocarbon solvents, which constitute the mixed solvent to be used as the reaction medium in the process according to the first aspect of this invention, include monochloro-, dichloro- or trichloro-($C_1$~$C_2$)alkane, preferably methylene chloride (namely, dichloromethane) or chloroform, or dichloroethane, or a mixture of two or more of them.

The other component of the mixed solvent to be used in the process of this invention is a lower alkanol. The lower alkanol may include an alkanol of 1~6 carbon atoms, preferably methanol, ethanol, n-propanol, isopropanol, n-butanol or t-butanol, or a mixture of two or more of them. Particularly preferred mixed solvent to be used is a mixture consisting essentially of chloroform and n-propanol.

In the process according to this invention, there is used as the reaction medium a mixed solvent made of a mixture of the chlorinated hydrocarbon solvent(s) with the alkanol solvent(s) as mixed together at a mix ratio (by volume) in a range of 1:3~1:0.25. Such a mixed solvent made of the mixture of the chlorinated hydrocarbon with the alkanol having the mix ratio preferably in a range of 1:1~1:0.28, more preferably 1:0.5~1:0.4 is desirably used. When the mix ratio of the chlorinated hydrocarbon to the alkanol present in the mixed solvent as employed is outside of the range of 1:3~1:0.25, the amount of the E-isomer as produced increases, while the amount of the Z-isomer as produced decreases. The reaction temperature used also influences largely on the amount of the Z-isomer as produced. In the process of this invention, the reaction is carried out at a reaction temperature in the range of +5° C.~−50° C., particularly of 0° C.~−50° C. Particularly, when the reaction is carried out at a temperature in the range of −10° C.~−30° C., the amount of the E-isomer as produced remarkably decreases, so that the amount of the Z-isomer as produced can be very much greatly improved as compared with that of the E-isomer.

Good results are given if the process according to the first aspect of this invention is practised in such a manner that the mix ratio (by volume) of the chlorinated hydrocarbon solvent and the lower alkanol in the mixed solvent as used is set in the range of 1:1~1:0.28, more preferably in the range of 1:0.5~−1:0.4, andalso that the reaction of a compound of formula (I) (or I') with a compound of formula (III) is effected at a temperature in the range of −10° C.~−30° C., preferably −18° C.~−23° C. Further, there is obtained such result that the amount of the Z-isomer produced is outstandingly improved as compared with that of the E-isomer, when the process according to the first aspect of this invention is carried out to conduct the reaction in a mixed solvent consisting of chloroform or dichloromethane and n-propanol as mixed at a mix ratio (by volume) in the range of 1:0.25~1:0.4, at a temperature in the range of −18° C.~−23° C.

The process according to the first aspect of this invention may conveniently be practised by dissolving the compound of formula (I) or (I') in the mixed solvent as used; cooling the resulting solution to a reaction temperature required; adding to the cooled solution a carbaldehyde of formula (III) in an amount stoichiometrically required or in excess or in large excess; stirring the resulting reaction mixture while maintaining the reaction mixture at the required low reaction temperature to effect the reaction for 12 ~20 hours.

After the completion of the reaction, the resulting reaction solution is washed with an aqueous potassium pyro-sulfite solution added, at need, to eliminate the residual aldehyde compound. Further, if the carbaldehyde compound of formula (III) has incidentally been reacted with the amino group of the compound of formula (I) to form a Schiff base, it is preferred to add an ethanol solution of Girard reagent to the reaction solution in order to decompose the Schiff base.

The reaction solution, which has been pre-treated as above, is then washed with an aqueous sodium chloride solution and then concentrated by evaporating the solvent under a reduced pressure or atmospheric pressure. To the resulting concentrated solution or solid residue is added methanol, ethyl acetate or butyl acetate, and the resultant mixture is allowed to stand for a certain time to deposit the desired Z-isomer by crystallization. At this time, the presence of a small amount or a very small amount of the E-isomer by-produced has no bad influence on the crystallization of the Z-isomer. Thus, the crystals of the Z-isomer so obtained are of a high purity. Therefore, no further purification step(s) such as recrystallization and chromatography is required to remove the E-isomer.

Further, we have carried out, as one example of the process according to the first aspect of this invention, such experiment in which 7-phenylacetamido-3-[(triphenyl-phosphoranyl-idene)methyl]-3-cephem-4-carboxylic acid 4-methoxybenzyl ester as one example of the compound of formula (I) was dissolved in a mixed solvent consisting of a mixture of methylene chloride and n-propanol at the mix ratio (by volume) of 1:0.4, followed by adding to the resultant solution 4-methylthiazol-5-yl-5-carbaldehyde, and reacting the resulting reaction mixture at a reaction temperature of −20° C.±2° C. for 14 hours under stirring (see Example 3 hereinafter given). After the completion of the reaction, the resulting reaction solution was subjected to a high performance liquid chromatography (HPLC) to determine the quantitative ratio of the Z-isomer to E-isomer of 7-phenylacetamido-3-[2-(4-methylthiazol-5-yl)vinyl]-3-cephem-4-carboxylic acid 4-methoxybenzyl ester as produced in the reaction solution. The conditions for the determination by HPLC are as follows:

Column: YMC A-312; Diameter 6.0 mm×Height 150 mm

Mobile phase: 0.05M phosphate buffer solution-acetonitrile (1:1)

Wave length of detecting light: 274 nm

It was found that the value of the ratio (Z:E) of the area (Z) under the absorption peak of the Z-isomer to the area (E) under the absorption peak of the E-isomer measured in the chromatogram so obtained was 45.4:1. An authentic sample of each of the Z-isomer and E-isomer was prepared by another route and HPLC data of these samples were prepared further. Taking the HPLC data so prepared into consideration, the value of the ratio (Z:E) of 45.1:1 for the rc.tio of the area (Z) to the area (E) defined above was assessed, revealing that the weight ratio of the Z-isomer to E-isomer present in the aforesaid reaction solution obtained in the above experiment was 94.6:5.4.

By way of comparison, the experiment just above was repeated except that the reaction temperature was set in the range of +25° C.±2° C. in place of the reaction temperature in the range of −20° C.±2° C. The resulting reaction solution obtained here was determined by HPLC in the same manner as above. Upon calculation from the numerical data of the area ratio (Z:E) of the area (Z) under the absorption peak of Z-isomer to the area (E) under the absorption peak of E-isomer measured in the chromatogram so obtained in the comparative experiment, it was found that the amount of the E-isomer present in the reaction solution as obtained in the comparative experiment was considerably larger in comparison with the amount of the Z-isomer present therein.

Although the experiments given above are merely an illustration, the above test results of these experiments may support that the Z-isomer can be remarkably produced preferentially to the E-isomer in accordance with the process of this first aspect invention.

Incidentally, when the 3-vinyl-3-cephem compound of general formula (IV) as produced by the process according to the first aspect of this invention has the residual amino-protecting group or/and the residual carboxyl-protecting group, such protecting group may be removed by a conventional means. Then, when the deprotected product desired has been recovered in a usual way out of the reaction solution coming from the above-mentioned deprotecticn reaction, it is still possible that the Z-isomer in the form of the deprotected product can be obtained at a high purity.

We, the inventors of this invention, have prosecuted our investigations further. As a result, we have found, that when the process according to the first a.spect of this invention is carried out with choosing methylene chloride or chloroform as the chlorinated hydrocarbon solvent to be used in the mixed solvent and with choosing n-propanol as the lower alkanol, and also when the reaction between the compound of formula (I) and the compound of formula (III) is effected in such particular mixed solvent of the mixture of the above two solvents mixed at the mix ratio (by volume) in the range of 1:1~1:0.28, and is effected particularly at a temperature in the range of –10° C.~–30° C., the amount of the Z-isomer of the product of formula (IV) as produced in the resulting reaction solution is considerably increased much than that of the E-isomer. Further, we have found that when the reaction solution so obtained is subjected to the under-mentioned post-treatments to recover the Z-isomer therefrom, crystals of the Z-isomer as harvested can be obtained at a high purity and in a high yield.

According to a second aspect of this invention, therefore, there is provided a process for the production of a highly pure Z-isomer of a 7-N-unsubstituted or substituted-amino-3-[2-(4-substituted or unsubstituted-thiazol-5-yl)vinyl]-3-cephem-4-carboxylic acid or an ester thereof having the formula (IV) above, which process comprises reacting a 7-N-unsubstituted or substituted-amino-3-[(tri-substituted phosphoranylidene) methyl]-3-cephem-4-carboxylic acid or an ester thereof having the following general formula (I)

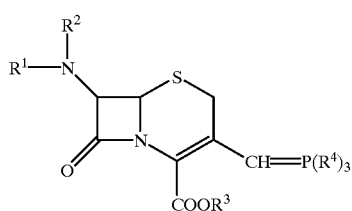

(I)

wherein $R^1$ denotes a hydrogen atom or a mono-valent amino-protecting group, or $R^1$ denotes a 2-(2-N-protected or unprotected-aminothiazol-4-yl)-2-alkoxyiminoacetyl group of the following formula (II)

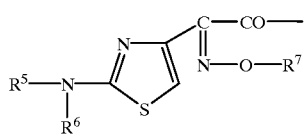

(II)

where $R^5$ is a hydrogen atom or a mono-valent amino-protecting group and $R^6$ is a hydrogen atom, or $R^5$ and $R^6$ as taken together mean one di-valent amino-protecting group, and $R^7$ is an alkyl group of 1~4 carbon atoms, and wherein $R^2$ denotes a hydrogen atom, or $R^1$ and R2 as taken together mean one di-valent amino-protecting group and $R^3$ denotes a hydrogen atom pivaloyloxymethyl group or an ester-forming group as a carboxyl-protecting group and $R^4$ denotes an alkyl group of 1~6 carbon atoms or an aryl group, or a compound represented by the following general formula (I')

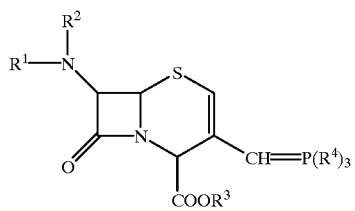

(I')

where $R^1$, $R^2$, $R^3$ and $R^4$ have the same meanings as defined above, with a 4-substituted or unsubstituted-thiazol-5-carbaldehyde represented by the following formula (III)

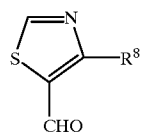

(III)

where $R^8$ denotes a hydrogen atom, an alkyl group of 1~4 carbon atoms, trifluoromethyl group or chlcoro group, in a mixed solvent consisting of a mixture of methylene chloride, chloroform or dichloroethane with n-propanol as mixed at a mix ratio (by volume) in a range of from 1:1 to 1:0.28, at a temperature in the range of –10° C. to –30° C., thereby to obtain the reaction solution containing the Z-isomer of the 7-N-unsubstituted or substituted-amino-3-[2-(4-substituted or unsubstituted-thiazol-5-yl)vinyl]-3-cephem-4-carboxylic acid or an ester thereof having formula (IV)

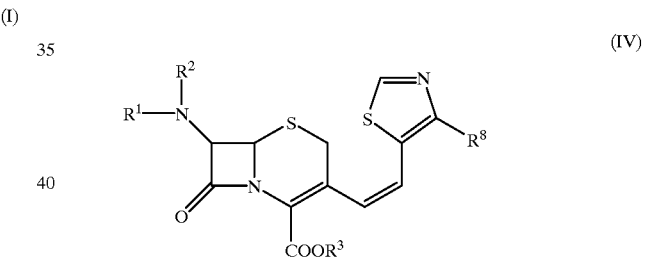

(IV)

where $R^1$, $R^2$, $R^3$ and R8 have the same meanings as defined above, then washing said reaction solution with an aqueous potassium pyrosulfite solution, thereafter concentrating the reaction solution, adding to the resulting concentrated solution methanol or butyl acetate or a mixture thereof so as to crystallize the Z-isomer of the compound of formula (IV) out of the solution.

In the process according to the second aspect of this invention, the reaction between the starting compound of formula (I) or (I') and the carbaldehiyde compound of formula (III) can be carried out in quite the same manner as that for the corresponding reaction in the process according to the first aspect of this invention. Further, in the process according to the second aspect of this invention, the crystals of the Z-isomer can be obtained by the step of crystallizing the Z-isomer from methanol or butyl acetate added to the said concentrated solution, and the crystals of the Z-isomer so obtained are containing only a very small amount of the E-isomer. Thus, the Z-isomer so obtained is in the form of highly pure crystals of the Z-isomer, and in most cases, it requires no further purification.

As is clear from the above, this invention is particularly useful for the preparation of 3- (2-substituted-vinyl)- cephlosporin antibiotics and also for the preparation of intermediates to be used For the synthesis of said cephalosporin antibiotics.

Best Mode for Carrying Out the Invention

The following Examples illustrate more concretely this invention, but not limit this invention thereto.

By the way, in the Examples given below, either the reaction solution containing the Z-isomer and E-isomer of the compound of formula (IV) as formed, or the other solutions were subjected to HPLC in order to assess the ratio between these Z- and E-isomers. The conditions used for the HPLC determination are the same as those used for the HPLC determination described hereinbefore, which are as follows:

Column: YMC A-312; Diameter 6.0 mm×Height 150 mm
Mobile phase: 0.05M phosphate buffer solution-acetonitrile (1:1 by volume)
Wave length of detecting light: 274 nm

EXAMPLE 1

(a) In a heterogeneous reaction medium consisting of chloroform(30 ml) andwater (30 ml), were dissolved 4-methoxy-benzyl 7-(4-acetylaminobenzylideneimino)-3-chloromethyl-3-cephem-4-carboxylate (5 g), triphenylphosphine (2.7 g) and sodium iodide (1.5 g).

The resulting reaction mixture was subjected to a reaction under stirring at a temperature of 32±1° C. for 2.5 hours. The chloroform layer containing 4-methoxybenzyl 7-(4-acetylaminobenzylideneimino)- 3-triphenylphosphonium-methyl-3-cephem-4-carboxyldte iodide thus formed was then separated from the resulting reaction solution.

The chloroform layer so separated was cooled to 3±1° C., and then a cold aqueous NaOH solution (containing 0.51 g of NaOH dissolved in 30 ml of water) was added thereto. The resultant mixture was subjected to a reaction at about 3° C. for 30 minutes.

(b) The chloroform layer containing 4-methoxy-benzyl 7-(4-acetylaminobenzylideneimino)-3-[(triphenyl-phosphoranylidene) methyl]-3-cephem-4-carboxylate so formed was separated from the resulting reaction solution and then dried over magnesium sulfate.

The liquid volume of the chloroform in the chloroform layer so dried was adjusted to 54 ml by adding an appropriate amount of chloroform to the dried chloroform layer. The resulting chloroform solution of said 3-(triphenyl-phosphoranylidene)methyl-cephem compound so formed was cooled to −25° C.±2° C., to which 21.5 ml of n-propanol was then added. The mix ratio (by volume) of chloroform to n-propanol present in the resulting solution was 1:0.4.

To the said solution was added 4-methylthiazol-5-carbaldehyde (9.3 g), and the resulting reaction mixture was subjected to a reaction under stirring for 14 hours, while cooling it to −20° C.±2° C.

The resulting reaction solution was washed with an aqueous potassium pyrosulfite solution and an aqueous sodium chloride solution under ice-cooling and was then concentrated. The resulting concentrated solution was added with methanol to effect crystallization of the target product, so that there were harvested crystals (2.51 g; yield 43.8 %) of 4-methoxybenzyl 7-(4-acetyl-aminobenzylideneimino)-3-[2-(4-methyl-thiazol-5-yl)vinyl]-3-cephem-4-carboxylate. The crystals were dissolved in methylenia chloride-acetonitrile, and the resulting solution was analyzed by HPLC under the same conditions as mentioned above. It was thus observed that the ratio of the area under the absorption peak of Z-isomer to the area under the absorption peak of E-isomer was 32.3:1. As evaluated from this numerical value of the area ratio (Z:E), it is shown that the amount of the E-isomer is very small in comparison with that of the Z-isomer.

$^1$H-NMR data of the above compound as harvested in this

EXAMPLE ARE SHOWN BELOW.

$^1$H-NMR: δ(CDCl$_3$)
2.18(3H, d, J=7.0 Hz)
2.41(3H,s)
2.24(1H, d, J=18.3 Hz)
3.49(1H, d, J=18.3 Hz)
3.78(3H,s)
5.10(1H, d, J=12.1 Hz)
5.15(1H, d, J=12.1 Hz)
5.23(1H, d, J=5.1 Hz)
5.41(1H, d, J=5.1 Hz)
6.30(1H, d, J=11.7 Hz)
6.54(1H, d, J=11.7 Hz)
6.79–7.82(8H, m)
8.58(1H,s)
8.78(1H,s)

EXAMPLE 2

(a) As the starting compound was used 4-methoxybenzyl 7-[(Z)-2-(2-tritylaminothiazol-4-yl)-2-methoxyiminoacetamido]-3-chloromethyl-3-cephem-4-carboxylate (2.6 g). This compound was reacted with triphenylphosphine and sodium iodide in the same manner as in Example 1(a). The resulting reaction product was treated with a cold aqueous NaOH solution in the same way as in Example 1(a).

(b) There was thus obtained a chloroform layer containing 4-methoxybenzyl 7-[(Z)-2-(2-trityleiminothiazol-4-yl)-2-methoxy-iminoacetamido]-3-[(triphenylphosphoranylidene) methyl]-3-cephem-4-carboxylate. Then, this 3-(triphenyl-phosphoranylidene)methyl-3-cephem compound was reacted with 4-methylthiazol-5-carbaldehyde in a mixed solvent made of a mixture of chloroform with n-propanoL (1:0.4)at a temperature in the range of −20° C.±2° C. for 14 hours in the same manner as in Example 1(b).

Thus, there were harvested crystals (2.30 g; yield:80.8%) of 4-methoxybenzyl 7-[(Z)-2-(2-tritylaminothiazol-4-yl)-2-methoxyiminoacetamido]-3-[2-(4-methylthiazol-5-yl)vinyl]-3-cephem-4-carboxylate. The resulting product was subjectedtoHPLCunder the same conditions as above-mentioned. The result of the HPLC analysis showed that the ratio of the area under the absorption peak of the Z-isomer to the area under the absorption peak of the E-isomer in the chromatogram obtained for the above product was 21.3:1.

$^1$H-NMR: δ(CDC13)
2.42(3H,s)
2.24(1H, d, J=18.7 Hz)
3.48(1H, d, J=18.7 Hz)
3.80(3H,s)
4.07(3H,s)
5.09(1H, d, J=12.0 Hz)
5.13(1H, d, J=12.0 Hz)
5.98(1H, m)
6.29(1H, d, J=11.7 Hz)
6.59(1H, d, J=11.7 Hz)
6.81–7.71(19H,m)
8.58(1H,s)

EXAMPLE 3

As the starting material was used 4-methoxybenzyl 7-phenylacetamido-3-chloromethyl-3-cephem-4-carboxylate (10.5 g). The reaction of this cephem compound with the reagents and the post-treatments of thre reaction products were carried out in the same manner as in Example 1(a) and (b). There were thus harvested crystals (10.2 g; yield: 90.9 %) of 4-methoxybenzyl 7-phenylacetamidto-3-[2-(4-methyl-thiazol-5-yl)vinyl]-3-cephem-4-carboxylate.

This product so harvested was analyzed by subjecting it to HPLC under the same measuring conditions as in those above-mentioned. As a result, it was found that the ratio of the area under the absorption peak of the Z-isomer to the area under the absorption peak of the E-isomer in the chromatogram obtained for said product was 45.4:1. From this numerical value, the weight ratio of the Z-isomer to theE-isomer present in said product was calculated to be 17.4:1, of which ratio correspond to 94.6:5.4 by numerical conversion. It can be seen from this that the proportion of the E-isomer in the harvested product is extremely small as compared with that of the Z-isomer.

$^1$H-NMR: $\delta(CDC_{13})$
2.40(3H,s)
3.21(1H, d, J=18 Hz)
3.46(1H, d, J=18 Hz)
3.67(2H, d J=3.5 Hz)
3.81(3H,s)
5.06(1H, d, J=5 Hz)
5.07(1H, d, J=5 Hz)
5.15(1H, d, J=12 Hz)
5.88(1H, dd, J=5 Hz and 9 Hz)
6.30(1H, d, J=12 Hz)
6.56(1H, d, J=12 Hz)
6.8–7.4(9H,m)
8.60(1H,s)

EXAMPLE 4

As the starting material was used t-butyl 7-phenylacetamido-3-bromomethyl-3-cephem-4-carboxylate (2.8 g). The reaction of this cephem compound with the reagents and the post-treatments of the reaction products were carried out in the same manner as in Example 1(a) and (b). Thus, there were harvested crystals (0.54 g; yield: 54.3%) of t-butyl 7-phenylacetamido-3-[2-(4-methylthiazol-5-yl)vinyl]-3-cephem-4-carboxylate.

This product so harvested was analyzed by subjecting it to HPLC under the same measuring conditions as in those abovementioned. As a result, it was found that the ratio of the area under the absorption peak of the Z-isomer to the area under the absorption peak of the E-isomer in the chromatogram obtained for said product was 29.4:1. From this numerical value, the weight ratio of the Z-isomer to the E-isomer present in said product was calculated to be 11.5:1, of which ratio correspond to 92:8 by numerical conversion. It can be seen from this that the proportion of the E-isomer in the harvested product is extremely small as compared with that of the Z-isomer.

$^1$H-NMR: $\delta(CDCl_3)$
1.35(9H,s)
2.44(3H,s)
3.18(1H, d, J=18.3 Hz)
3.44(1H, d, J=18.3 Hz)
3.65(2H, d, J=2.6 Hz)
5.05(1H, d, J=4.8 Hz)
5.87(1H, m)
6.29(1H, d, J=11.7 Hz)
6.61(1H, d, J=11.7 Hz)
7.26~7.71(5H, m)
8.61(1H,s)

EXAMPLE 5

(a) 4-methoxybenzyl 7-amino-3-chloromethyl-3-cephem-4-carboxylate (1.1 g), triphenylphosphine (0.55 g) and sodium iodide (0.32 g) were dissolved in a heterogeneous reaction medium consisting of chloroform (6.5 ml) and water (6.5 ml). The resulting reaction mixture was subjected to the reaction at a temperature of 32° C.±1° C. for 2 hours. The chloroform layer containing the resulting reaction product desired was separatedfromthereactionsolutionasformed. Aftercooling the chloroform layer so separated to 3±10° C., a cold aqueous NaOH solution (containing 0.17 g of NaOH dissolved in 8.6 ml of water) was added to the cooled chloroform layer, with which the further reaction was conducted at a temperature of 3±1° C. for 1 hour and 15 minutes.

(b) A chloroform layer containing 4-methoxybenzyl 7-amino-3-[(triphenylphosphoranylidene)methyl]-3-cephem-4-carboxylate so produced was separated form the resulting reaction solution. The chloroform layer so separated was dried over magnesium sulfate, and ther. an amount of chloroform was added thereto to adjust the liquid volume of chloroform present in said chloroform layer to 12 ml. The resulting solution was cooled to 25° C.±2° C., to which was then added 4.6 ml of n-propanol, followed by further addition of 1.9 g of 4-methylthiazol-5-carbaldehyde. The mix ratio of chloroform to n-propanol in the resulting reaction mixture was 1:0.38 (by volume). The reaction mixture was cooled to −20° C.±2° C. and subjected to the reaction at −20° C.±2° C. under stirring.

After the completion of the reaction, the reaction solution as obtained was washed with an aqueous potassium pyrosulfite solution under ice-cooling and was then reacted with Girard reagent Tat 22° C. for 1 hour after adding an ethanol solution (6.7 ml) of Girard reagent T (0.67 g). The resulting reaction solution was washed with an aqueous sodium chloride solution and then concentrated. Crystallization of the reaction product was effected by adding butyl acetate to the resulting concentrated solution. Thus, there were harvested crystals (0.50 g; yield: 56.0%) of 4-methoxybenzyl 7-amino-3-[2-(4-methylthiazol-5-yl)vinyl]-3-cephem-4-carboxylate.

This product so harvested was analyzed by subjecting it to HPLC under the same measuring conditions as those mentioned above. As a result, it was found that the ratio of the area under the absorption peak of the Z-isomer to the area under the absorption peak of the E-isomer in the chromatogram obtained for the harvested product was 31.9:1. From this numerical value, the weight ratio of the Z-isomer to the E-isomer present in said product was calculated to be 13.3:1, of which ratio correspond to 93:7 by numerical conversion. It can be seen from this that the proportion of the E-isomer in the harvested product is extremely small as compared with that of the Z-isomer.

$^1$H-NMR: $\delta(DMSO-d_6)$
2.43(3H,s)
2.54(2H,s)
3.79(3H,s)
5.15(2H, d, J=4.3 Hz)
5.22(1H, d, J=5.1 Hz)
5.32(1H, d, J=5.1 Hz)
6.58(1H, d, J=12.1 Hz)
6.80(1H, d, J=12.1 Hz)
9.59(1H,s)

EXAMPLES 6~25

(a) 4-Methoxybenzyl 7-phenylacetamido-3-chloromethyl-3-cephem-4-carboxylate (6 g), triphenylphosphine (3.4 g) and sodium iodide (1.94 g) were dissolved in a heterogeneous reaction medium consisting of a chlorinated hydrocarbon solvent (36 ml) as listed in Table 1 below and water (36 ml). The resultant reaction mixture was subjected to the reaction at a temperature of 32° C.±1° C. for 1.5 hours. After confirming the disappearance of the starting material, the organic layer was separated from the resulting reaction solution and then cooled to 3±1° C. Thereafter, a cold aqueous NaOH solution (containing 0.64 g of NaOH dissolved in 36 ml of water) was added to the cooled organic layer, with which the further reaction was then conducted at a temperature of 3±1° C. for 30 minutes.

(b) After confirming the disappearance of the starting material, the organic layer containing 4-methoxybenzyl 7-phenyl-acetamido-3-[(triphenylphosphoranylidene)methyl]-3-cephem-4-carboxylate so produced was separated from the resulting reaction solution and then dried over magnesium sulfate. The organic layer so dried was cooled to the respective reaction temperature shown in Table 1.

After cooling, said organic layer was added with an alkanol solvent as listed in Table 1 so that the alkanol as added and the chlorinated hydrocarbon solvent were made to be present in the resultant mixture, in the particular proportions (by volume) of them as shown in Table 1. Further, 4-methyl-thiazol-5-carbaldehyde (11.8 g) was added to the organic phase. The resulting mixture was then subjected to the reaction at a reaction temperature as shown in Table 1 for 14 hours. After the completion of the reaction, the reaction solution so obtained was subjected to HPLC. analysis in order to determine the proportion of the Z-isomer and E-isomer of 4-methoxybenzyl 7-phenylacetamido-3-[2-(4-methylthiazol-5-yl)vinyl]-3-cephem-4-carboxylate as produced in said reaction solution. The conditions used for the determination by the HPLC. analysis were the same as those mentioned above.

The reaction conditions used and the experiment results obtained in Examples 6~25 are summarily shown in Table 1(a) below. In the table, BtOH shows butanol, PrOH shows propanol and MeOH shows methanol.

Comparative Examples 1~2

By way of comparison, the reaction of the triphenylphosphoranylidene-methyl cephem compound with 4-methylthiazol-5-carbaldehyde as illustrated in Examples 6~25 was carried out at room temperature (25° C.±2° C.) for 14 hours in the same manner as in Examples 6~25. After the completion of the reaction, the ratio of the Z-isomer to E-isomer present in the reaction solution as obtained here was measured by HPLC. analysis in a similar way.

The results of Comparative Examples 1~2 are also shown in Table 1(b) below. These results of Table 1(b) clearly show that the proportions of the Z-isomer and E-isomer present in the product compound as obtained are largely differentiated, depending upon the mixed solvent used and the reaction temperature used. In particular, if the reaction is effected at a temperature of −20° C.±2° C., the area ratio of the Z-isomer to E-isomer under the absorption peak of HPLC chromatogram of the reaction product, can reach such values that the area of the Z-isomer was 20 times or more and sometimes 30 times or more higher than the area of the E-isomer. Accordingly, the processes of this invention evidently can achieve the selective production of the Z-isomer.

TABLE 1(a)

| Example No. | Mixed solvent (Mix ratio, by volume) | | Reaction temperature (° C.) | Area ratio (Z:E) under the absorption peaks of Z-isomer to E-isomer in the chromatogram of HPLC of the reaction solution |
|---|---|---|---|---|
| 6 | CH$_2$Cl$_2$—BtOH | (1:3) | +3° C. ± 2° C. | 14.8:1 |
| 7 | CH$_2$Cl$_2$—BtOH | (1:1) | +3° C. ± 2° C. | 16.9:1 |
| 8 | CH$_2$Cl$_2$-isoPrOH | (1:1) | +3° C. ± 2° C. | 17.5:1 |
| 9 | CH$_2$Cl$_2$-n-PrOH | (1:1) | +3° C. ± 2° C. | 17.9:1 |
| 10 | CH$_2$Cl$_2$-n-PrOH | (2:1) | +3° C. ± 2° C. | 19.9:1 |
| 11 | CH$_2$Cl$_2$-n-PrOH | (4:1) | +3° C. ± 2° C. | 18.7:1 |
| 12 | CH$_2$Cl$_2$-t-BuOH | (4:1) | +3° C. ± 2° C. | 16.9:1 |
| 13 | CH$_2$Cl$_2$—BtOH | (2:1) | −20 ± 2 | 19.9:1 |
| 14 | CH$_2$Cl$_2$-n-PrOH | (3:2) | −20 ± 2 | 19.2:1 |
| 15 | ClCH$_2$CH$_2$Cl-n-PrOH | (2:1) | −20 ± 2 | 16.2:1 |
| 16 | CH$_2$Cl$_2$-n-PrOH | (7:2) | −20 ± 2 | 20.2:1 |
| 17 | CH$_2$Cl$_2$-n-PrOH | (3:1) | −20 ± 2 | 21.6:1 |
| 18 | CH$_2$Cl$_2$-n-PrOH | (2:1) | −20 ± 2 | 23.5:1 |
| 19 | CH$_2$Cl$_2$-t-BuOH | (2:1) | −20 ± 2 | 25.8:1 |
| 20 | CH$_2$Cl$_2$-n-PrOH | (5:2) | −20 ± 2 | 28.8:1 |
| 21 | CHCl$_3$-n-PrOH | (2:1) | −20 ± 2 | 25.0:1 |
| 22 | CHCl$_3$-n-PrOH | (5:2) | −20 ± 2 | 31.0:1 |
| 23 | CHCl$_3$-n-PrOH | (3:1) | −20 ± 2 | 29.8:1 |
| 24 | CHCl$_3$-n-PrOH | (7:2) | −20 ± 2 | 26.8:1 |
| 25 | CHCl$_3$-n-PrOH | (4:1) | −20 ± 2 | 27.0:1 |

TABLE 1(b)

| Comparative Example No. | Mixed solvent (Mix ratio, by volume) | | Reaction temperature (° C.) | (Z:E) |
|---|---|---|---|---|
| 1 | CH$_2$Cl$_2$—MaOH | (1:8) | 25° C. ± 2° C. | 4.2:1 |
| 2 | CH$_2$Cl$_2$—BtOH | (1:3) | 25° C. ± 2° C. | 8.0:1 |

Industrial Applicability

As is clear from the foregoing, it is seen that, according to the processes of this invention, when a 3-(2-substituted vinyl)-cephem compound is to be produced by utilizing the Wittig's reaction, the Z-isomer of said cephem compound can be produced in a considerably larger proportion than that of the E-isomer, that is, preferentially and in a high yield. The processes of this invention can be practised in a facile way and efficiently. The target product compound obtained by the processes of this invention has only an extremely small content of the E-isomer, as compared with the content of the desired Z-isomer. The processes according to this invention are useful for the production of a 3-(Z)-(2-substituted vinyl)-cephalosporin antibiotic excellent as antibacterial agent, or for the production of intermediates for use in the synthesis of said antibiotic.

What is claimed is:

1. A process for the production of the Z-isomer of a 7-N-unsubstituted or substituted-amino-3-[2-(4-substituted or unsubstituted-thiazol-5-yl)vinyl]-3-cephem-4-carboxylic acid or an ester thereof represented by the following formula (IV)

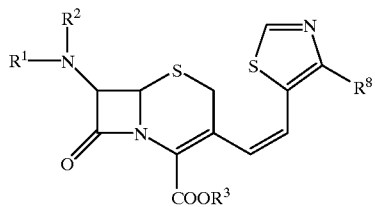

(IV)

wherein $R^1$ denotes a hydrogen atom or a mono-valent amino-protecting group, or $R^1$ denotes a 2-(2-N-protected or unprotected-aminothiazol-4-yl)-2-alkoxyiminoacetyl group having the following formula (II)

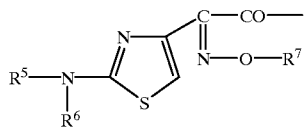

(II)

where $R^5$ is a hydrogen atom or a mono-valent amino-protecting group and $R^6$ is a hydrogen atom, or $R^5$ and $R^6$ as taken together mean one di-valent amino-protecting group and $R^7$ is an alkyl group of 1 to 4 carbon atoms, and wherein $R^2$ denotes a hydrogen atom, or $R^1$ and $R^2$ as taken together mean one di-valent amino-protecting group and $R^3$ denotes a hydrogen atom, a pivaloyloxymethyl group or an ester-forming group as a carboxyl-protecting group, and $R^8$ denotes a hydrogen atom, an alkyl group of 1 to 4 carbon atoms, a trifluoromethyl group or a chloro group, wherein said process comprises reacting a 7-N-unsubstituted or substituted-amino-3-[(tri-substituted-phosphoranylidene)methyl]-3-cephem-4-carboxylic acid or an ester thereof represented by the following formula (I)

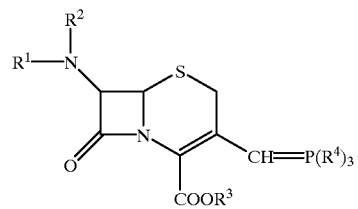

(I)

where $R^1$, $R^2$ and $R^3$ each have the same meanings as defined above and $R^4$ denotes an alkyl group of 1 to 6 carbon atoms or an aryl group, or a compound represented by the following formula (I')

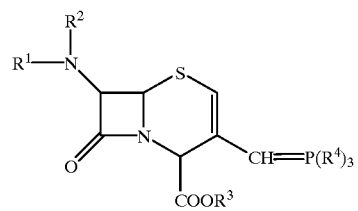

(I')

where $R^1$, $R^2$, $R^3$ and $R^4$ each have the same meanings as defined above, with a 4-substituted or unsubstituted-thiazol-5-carbaldehyde represented by the following formula (III)

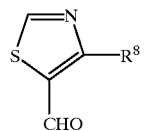

(III)

where $R^8$ has the same meaning as defined above, in a mixed solvent consisting of one or more chlorinated hydrocarbon solvent(s) and one or more lower alkanol (s) mixed at a mix ratio (by volume) in a range of from 1:3 to 1:0.25, at a temperature of +5° C. to −50° C.

2. The process according to claim 1, wherein the reaction of a compound of formula (I) with a compound of formula (III) is effected at a temperature of 0° C. to −50° C.

3. The process according to claim 1, wherein the mix ratio of the chlorinated hydrocarbon solvent(s) to the lower alkanol(s) present in the mixed solvent as used is in the range of 1:1 to 1:0.28, and wherein the reaction of a compound of formula (I) with a compound of formula (III) is effected at a temperature in the range of −10° C. to −30° C.

4. The process according to claim 1, wherein the chlorinated hydrocarbon solvent is a monochloro-, dichloro- or trichloro- ($C_1$ to $C_2$) alkane.

5. The process according to claim 1, wherein the lower alkanol is an alkanol of 1 to 6 carbon atoms.

6. The process according to claim 1, wherein the reaction is effected in a mixed solvent consisting of a mixture of chloroform or methylene chloride with n-propanol as mixed at a mix ratio (by volume) in the range of 1:0.25 to 1:0.4, at a temperature in the range of −18° C. to −23° C.

7. A process for the production of a crystalline form of the Z-isomer of a 7-N-unsubstituted or substituted-amino-3-[2-

(4-substituted or unsubstituted-thiazol-5-yl)vinyl]-3-cephem-4-carboxylic acid or an ester thereof having the following formula (IV)

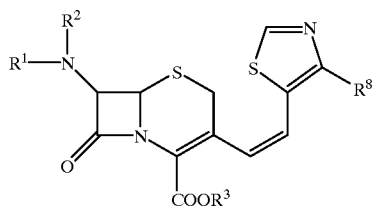
(IV)

wherein $R^1$ denotes a hydrogen atom or a mono-valent amino-protecting group, or $R^1$ denotes a 2-(2-N-protected or unprotected-aminothiazol-4-yl)-2-alkoxyiminoacetyl group of the following formula (II)

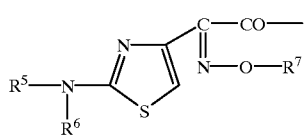
(II)

where $R^5$ is a hydrogen atom or a mono-valent amino-protecting group and $R^6$ is a hydrogen atom, or $R^5$ and $R^6$ as taken together mean one di-valent amino-protecting group and $R^7$ is an alkyl group of 1 to 4 carbon atoms, and wherein $R^2$ denotes a hydrogen atom, or $R^1$ and $R^2$ as taken together mean one di-valent amino-protecting group and $R^3$ denotes a hydrogen atom, a pivaloyloxymethyl group or an ester-forming group as a carboxyl-protecting group, and $R^8$ denotes a hydrogen atom, an alkyl group of 1 to 4 carbon atoms, a trifluoromethyl group or a chloro group, which process comprises reacting a 7-N-unsubstituted or substituted-amino-3-[(tri-substituted-phosphoranylidene)methyl]-3-cephem-4-carboxylic acid or an ester thereof having the following formula (I)

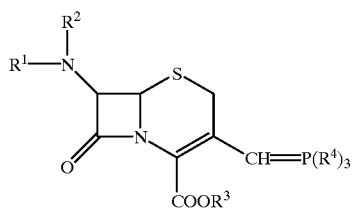
(I)

wherein $R^1$, $R^2$ and $R^3$ each have the same meanings as defined above and $R^4$ denotes an alkyl group of 1 to 6 carbon atoms or an aryl group, or a compound represented by the following formula (I')

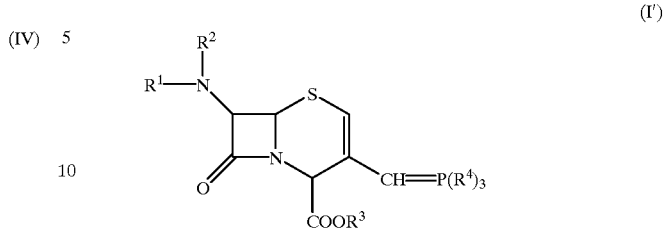
(I')

where $R^1$, $R^2$, $R^3$ and $R^4$ each have the same meanings as defined above, with a 4-substituted or unsubstituted-thiazol-5-carbaldehyde represented by the following formula (III)

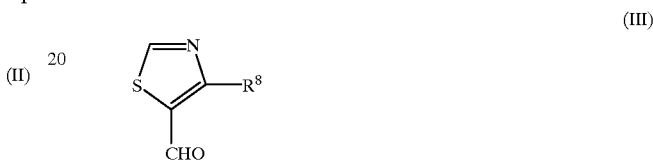
(III)

where $R^8$ has the same meaning as defined above, in a mixed solvent consisting of a mixture of methylene chloride, chloroform or dichloroethane with n-propanol at a mix ratio (by volume) in a range of from 1:1 to 1:0.28 at a temperature in the range of $-10°$ C. to $-30°$ C., thereby to obtain the reaction solution containing the Z-isomer of the 7-N-unsubstituted or substituted-amino-3-[2-(4-substituted or unsubstituted-thiazol-5-yl) vinyl]-3-cephem-4-carboxylic acid or an ester thereof of the formula (IV) above, then washing said reaction solution with an aqueous potassium pyrosulfite solution, thereafter concentrating the reaction solution, adding to the resulting concentrated solution methanol or butyl acetate or a mixture thereof so as to crystallize the Z-isomer of the compound of formula (IV) out of the solution.

8. The process according to claim 1, wherein the mix ratio of the chlorinated hydrocarbon solvent(s) to the lower alkanol(s) present in the mixed solvent as used is in the range of 1:0.5 to 1:0.4, and wherein the reaction of a compound of formula (I) with a compound of formula (III) is effected at a temperature in the range of $-18°$ C. to $-23°$ C.

9. The process according to claim 4, wherein the chlorinated hydrocarbon solvent is a methylene chloride, chloroform or dichloroethane, or a mixture of two or more of them.

10. The process according to claim 5, wherein the lower alkanol is methanol, ethanol, n-propanol, isopropanol, n-butanol or t-butanol, or a mixture of two or more of them.

* * * * *